United States Patent [19]
Weber et al.

[11] Patent Number: 5,782,249
[45] Date of Patent: Jul. 21, 1998

[54] LASER MANICURE PROCESS

[76] Inventors: Paul J. Weber, 5353 N. Federal Hwy., Suite 400, Ft. Lauderdale, Fla. 33308; Michael R. Weber, 100 W. Kennedy Blvd., Tampa, Fla. 33602; Robert Weber, 5353 N. Federal Hwy., Suite 400, Ft. Lauderdale, Fla. 33308

[21] Appl. No.: 724,182

[22] Filed: Sep. 30, 1996

[51] Int. Cl.$^6$ .................................................. A45D 24/00
[52] U.S. Cl. .......................... 132/200; 132/73; 132/285; 606/10; 606/16
[58] Field of Search ............... 132/200, 73, 73.5, 132/73.6, 75.3, 75.4, 285; 433/29, 25; 606/116, 2, 9, 10, 11, 13, 16, 17, 18, 19; 128/898, 395, 398

[56] References Cited

U.S. PATENT DOCUMENTS

| | | | |
|---|---|---|---|
| 4,270,845 | 6/1981 | Takizawa et al. | 606/2 |
| 5,118,293 | 6/1992 | Levy | 606/2 |
| 5,217,455 | 6/1993 | Tan | 606/2 |
| 5,522,813 | 6/1996 | Trelles | 606/9 |
| 5,526,372 | 6/1996 | Albrecht et al. | 372/69 |
| 5,586,981 | 12/1996 | Hu | 606/9 |
| 5,636,983 | 6/1997 | Shoji et al. | 433/29 |

*Primary Examiner*—Gene Mancene
*Assistant Examiner*—Pedro Philogene
*Attorney, Agent, or Firm*—John Lezdey

[57] ABSTRACT

There is provided an improved process and apparatus for cutting and/or fingernails. The process includes the step of providing laser radiation to cut or score the nails, and optionally cooling the site of administration of the laser beam. The nails can be coated with colored lacquers to provide a multicolored design when melted by the laser.

16 Claims, 2 Drawing Sheets

LASER MANICURE PROCESS

BACKGROUND OF THE INVENTION

1. Field Of The Invention

The present invention is directed to cutting and decorating fingernails with laser radiation. More particularly, there is provided a process utilizing laser radiation to provide an aesthetic appearance to nails.

2. Description Of The Prior Art

The application of lasers for therapeutic treatment of a variety of diseases and conditions is well known. Lasers have been used successfully for hemostasis, photodynamic destruction of some forms of tumors, removal of epidermal growths and abnormalities, and the like. However, no prior art discloses cutting fingernails with laser radiation. Generally, mechanical devices such as clippers and scissors are used for this procedure.

Furthermore, additional steps of filing and brushing may be necessary to accomplish the desired result. In some cases these operations and the use of these implements are difficult for persons which are disabled or may be arthritic. In commercial establishments, these operations are time consuming, tie-up operators limit the number of clients which can be attended which reduces profits.

In the elderly, the fingernails become ridged or lined. It is difficult in such cases to manicure or shape the nails with an emery board and/or sanding wheels. It is further desirable in such cases to soften the nails so as to work with them.

Therefore, it can be appreciated that there exists a continuing need for a new and improved simple and economical process for decorating and/or cutting fingernails which can be used commercially, as well as, for home use to obtain similar results. In this regard, the present invention substantially fulfills this need.

Washable tattoos are commercially sold which are applied to both toenails and fingernails. However, such tattoos are not useful or are lost at the beach or swimming pools.

It is understood that the term "fingernails" also relates to toe nails.

SUMMARY OF THE INVENTION

The present invention comprises a method for decorating and/or cutting or shaping fingernails with high energy laser radiation. The preferred method involves using a laser directing means which preferably include an articulated arm assembly comprising: an elongated tubular housing constructed to contain a radiation delivery end and enclosing a chamber which is inadjacent to the radiation delivery end; radiation conducting means disposed in the tubular housing for conducting laser radiation from a laser generating source toward the radiation delivery end; and means forming a gas flow path in the chamber for guiding a flow of cooling gas through the chamber in direction toward the radiation delivery end. Further, in a most preferred embodiment the human hand is secured in a template to immobilize the hand so that the laser cutting trims or decorates the fingernails more closely and evenly. The cooling agent can be generated from liquified nitrogen or solidified carbon dioxide.

More specifically, one preferred embodiment involves a method which comprises the steps of:

a) positioning a laser directing means including an articulated arm assembly containing a laser means having a laser generating source in communication with a radiation delivery means at the fingernail site; and b) energizing a laser beam of sufficient intensity to produce the desired cutting procedure and optionally, to simultaneously provide cooling means to said laser treatment site.

In the decorating procedure, one or more coatings of a colorant may be utilized to provide a colored design with the laser. Alternatively, a design can be imparted on the nail and then a suitable colorant utilized.

In accordance with another embodiment of the present invention the cooling means may be dispensed directly to the fingernail site and not through the radiation delivery means. Alternatively, the cooling means may be passed through both the laser delivery means and dispensed directly to the laser treatment site.

It is a primary object to provide a method for decorating and cutting fingernails using laser radiation at higher power levels.

Another object of the invention is to facilitate the efficient delivery of laser radiation to the fingernail site.

It is a further object to provide a means for cutting and/or shaping fingernails and/or toenails of patients.

It is another object to provide tattoo like decorations to the nails.

Still another object of the invention is to provide a method of cutting and/or decorating or shaping fingernails which increases the speed, efficiency and safety while providing a more precise and even fingernail shape or cut.

Other objects and many of the attendant advantages of this invention will be readily appreciated as the same become better understood by reference to the following detailed description when considered in conjunction with the accompanying drawings.

BRIEF DESCRIPTION OF THE INVENTION

DESCRIPTION OF THE PREFERRED EMBODIMENTS

Figure 1:
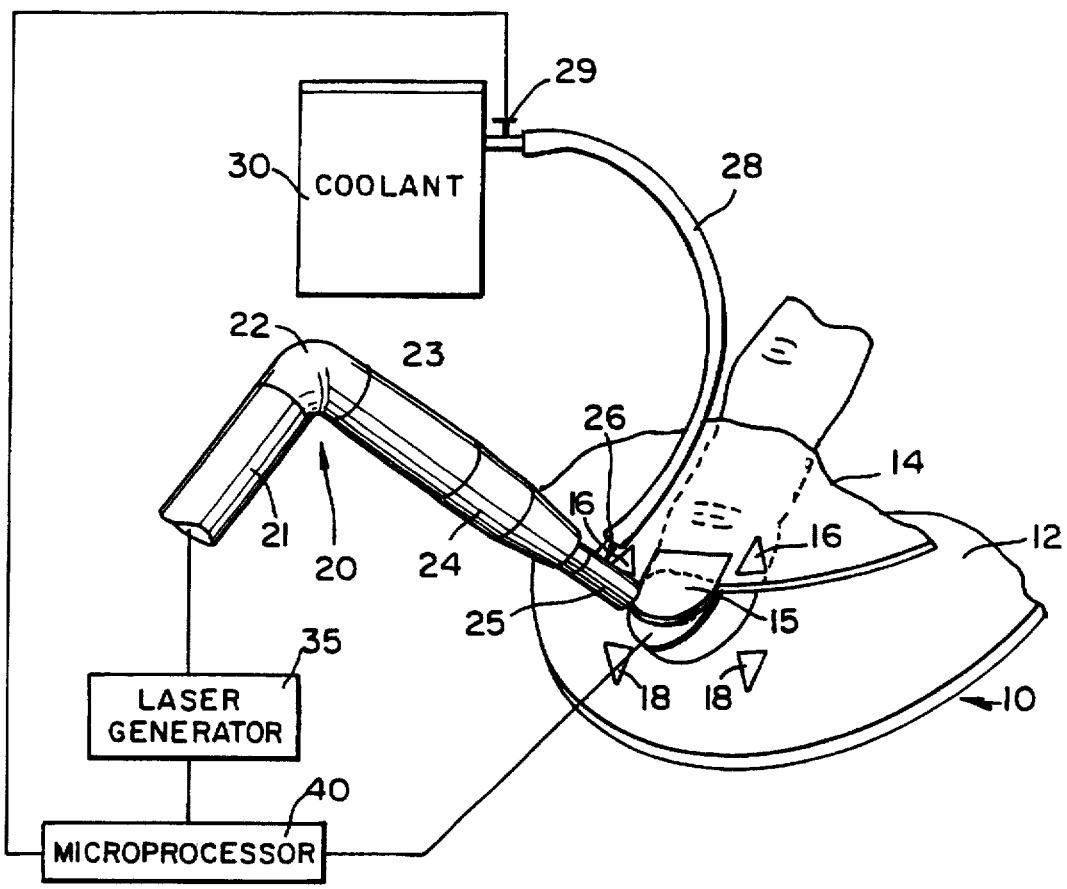
FIG. 1 is a partial perspective view showing laser means cutting a fingernail wherein the cooling step is accomplished by passing a coolant through the laser cutting tip with the finger placed in accordance with the present invention.

The present invention generally comprises a method for laser decorating and/or cutting fingernails. Referring to FIG. 1, a laser directing means 20 includes an articulated arm assembly which comprises a first tube 21, a rotatable elbow 22, a second tube 23, and a rotatable tube 24 which is in communication with laser cutting tip 25. Each of the tube components are preferably made of resilient stainless steel and are joined by welds to form a laser delivery system. The rotatable tube 24 may have a soft polymer cover to make more comfortable for hand adjustment. The proximal end of the laser directing means 20 is designed to receive the laser beam from a laser generator 35 controlled by a microprocessor 40. The distal end of the laser directing means 20 contains a laser cutting tip 25, which is to be positioned to administer laser radiation to the fingernail to be targeted. Further, in accordance with one embodiment of the present invention as shown in FIG. 1 a coolant fluid is supplied to the laser tip 25. Generally, the coolant fluid is an inert gas. Liquids can also be used but require removal and disposal from the cutting site. Suitable coolants include inert gases such as nitrogen, argon, carbon dioxide, and air. Inert gases are preferred since they do not pose a health hazard and are easily dissipated. Liquid nitrogen is the preferred coolant. A coolant storage tank 30 is connected through a gutted timed valve 29 and fluid conduit 28 to coolant inlet connector 26 thence to the laser cutting tip 25.

The present invention provides a method for cutting or scoring hard tissue such as fingernails comprising a laser beam provided with means enabling radiation to be emitted in form of pulsed or non-pulsed energy in sufficient number to deliver a total amount of energy that causes the cutting or scoring of the fingernails. The method being characterized in that it includes steps for adjusting the number and duration of the laser pulses in phase lag sequence of pulses of coolant to maintain a comfort level to the fingernail area, as well as, providing a safeguard to prevent overheating the laser cutting tip 25 and the delivery system if optical fibers are used. The energy level of the laser is adjusted according to cutting or decorating the fingernail.

In the cutting procedure, the laser can trim and/or shape the nails to be scalloped, rounded, etc. either by the skill of the operator or through a computer programmed mechanism (not shown).

The nails can be coated using one or more nail lacquers or pigments and then provided with a desirable decoration to one or more nails. The amount of laser energy can be adjusted so that only the coating layers and the nail itself are scored by the laser beam. A computerized and mechanized means can be employed to provide more complex designs. Commercial nitrocellulose containing nail lacquers, silver or gold flake inks, pearlite coatings, and the like are suitable coatings for decorating purposes.

Figure 2:
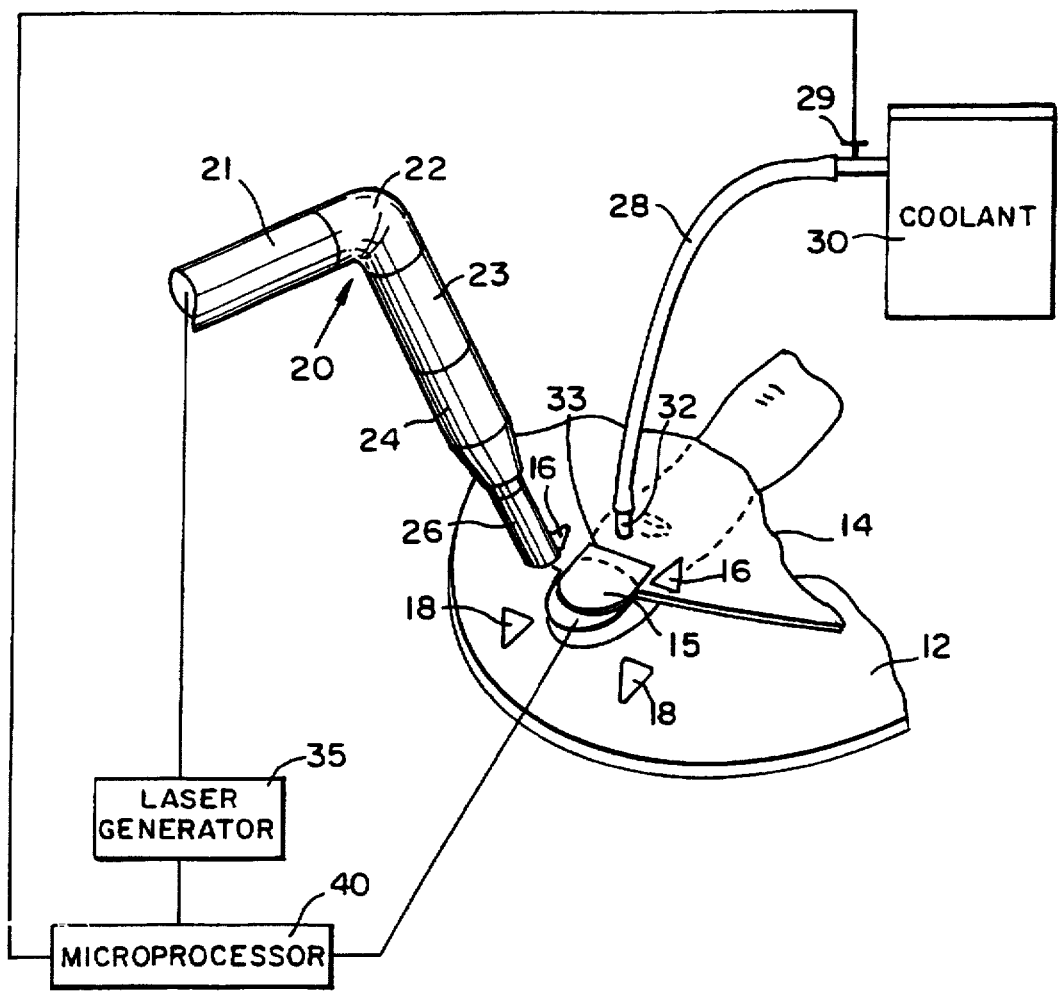
FIG. 2 is a partial perspective view showing laser means cutting a fingernail wherein the cooling step is accomplished by passing a coolant to a plate in contact with the skin with the finger secured in a template in accordance with the present invention.

FIG. 2 illustrates a preferred embodiment in a partial perspective view of a hand template known in the prior art and generally designated by reference numeral 10. In the broadest terms, the template 10 includes a lower template 12 and an upper template 14. The lower template 12 is configured to accept placement of a persons entire hand, although only a single finger is shown. The lower template 12 may be positioned in a horizontal plane. It is preferably fabricated of solid construction such as metal or plastics. The lower template 12 preferably has a representation of a human hand formed thereon by printing or painting and includes a plurality of positioning or alignment notches 16 and 18. An upper template 14 is also provided and may be positioned in a horizontal plane and configured to follow the top of a human hand. A person's hand is interposed between the top and bottom templates. The upper template 14 is further provided with a plurality of positioning or alignment notches 16 which are to be aligned with similar notches 18 on the lower template 12. In addition the top template 14 contain a plurality of openings 15 which correspond to the fingernail positions of the hand placed on the lower template 12. Openings 15 may be available in a variety of sizes.

In practice, a person places a hand to correspond to the position of the printed hand on the lower template 12. An upper template 14 having the required sizes of nail openings 15 is then positioned over the top of the hand lined up with the positioning or alignment 16 and 18 exposing the fingernail intended to be cut. The laser directing means 20 is also aligned with the specific fingernail to be treated. Standard precautions for the operator is taken such as wearing eye protection.

The laser means when energized is guided by hand gripping the rotatable tube 24 is drawn across and cuts the fingernail closely and evenly. The cut is so precise that filing or polishing is not required. The laser generator 35 provides a high energy laser beam with a power of about 1–5 watts pulsed at intervals of 0.5–2.0 seconds controlled by microprocessor 40 or non-pulsed. Likewise, the microprocessor monitors the temperature of the laser cutting tip 25, as well as, the temperature of the fingernail site. Based on this input data the microprocessor controls the gated time valve 29 to pulse the release of nitrogen gas generally 0.5 seconds after the laser beam pulse. Thus, these automatic controls make the fingernail site conformable and protect the equipment from overheating. The sequence is repeated for each fingernail. The cutting can be contained within the designated areas by having the microprocessor shut off the laser when comparison indicates that the wrong areas are about to be cut.

Suitable laser crystals include those capable of emitting laser radiation at about 1060 nm (nanometers) or 1320 nm, in particular, by using nedynium YAG (Nd-YAG) crystal or an erbium YAG (Er-YAG) crystal or a Holmium-YAG crystal.

In a further embodiment of the invention as shown in FIG. 3, the coolant may be dispensed directly to the fingernail site through coolant inlet plate 32 placed under the upper template 14. The amount of coolant provided the cutting site is controlled by microprocessor 40. In this embodiment, the cutting tip 27 is not incorporated in the cooling system. Overheating in this case is prevented in the laser generating system in which the microprocessor increases the duration between pulses.

In yet another embodiment of this invention, both the direct application of coolant, as well as, direct cooling of the laser cutting tip 25 can be integrated and controlled by microprocessor 40.

The invention herein will be illustrated by the following examples, but is not limited thereto.

EXAMPLE I

An elderly person having ridged and lined nails had his fingernails manicured by the procedure of the invention. The nails were first brushed and then soaked in water for one minute to provide moisture to the nails before using the laser. The water helps to control the perpetration of the laser and prevent deep passage of heat. The hand was then immobilized on a template. A Sharplan 40° C. carbon dioxide laser was used to ablate the nail ridges. The nails were trimmed using continuous non-pulsed energy at a 1 watt level using a 60 mm handpiece which was slightly defocused and had a passage at about 4 mm per second. The nails did not require use of an emery board.

The operation of the laser was according to ANSI 2136 series of laser safety standards of the Laser Institute of America, which is incorporated herein by reference.

EXAMPLE II

A laser manicure was performed so that the nails had a sculpted scalloped border with miniature partial outward portions of a circle. The nails of the person being manicured were coated with a clear acrylic coating composition which was commercially available as a nail lacquer. The procedure of Example I was followed except that the nails were not soaked in water and the beam was not defocused. The scalloping was manually performed by the laser operator.

If desired, the nails may have been coated with a plurality of colored coating layers and the laser may have been used to imprint a design.

EXAMPLE III

A design was placed on the fingernails of a person by first preparing a computer generated stencil. The design was enlarged and a motorized arm was used to translate the design onto a thickly lacquered fingernail which had a coating of white, red, orange and pink as the outermost layer. A Sharplan 40° C. carbon dioxide laser at a 1 watt energy level which was in a focus mode and the pulsed mode was used with an on time of 0.05 seconds and an off time of 0.5 seconds. Through different laser penetration and melt a multicolored design was obtained.

It is understood that the process of the invention may be varied by employing various known methods to apply the design or use the laser. For example, a heat responsive colorant may be used with varying wavelengths of energy, namely, a chromophore. Alternatively, a computer driven laser may be used to create a design.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method for cutting or decorating fingernails comprising the step of:
   a) positioning a laser directing means including an articulated arm assembly containing a laser having a laser generating source in communication with a laser radiation delivery means at the fingernail site; and
   b) selectively energizing a laser beam of sufficient intensity to produce the desired cutting or to score the fingernail itself or a coating on the nail in a decorating procedure.

2. The method of claim 1 wherein a cooling means is applied to the radiation delivery means.

3. The method of claim 1 wherein a cooling means is applied to the radiation delivery means and the fingernail site.

4. The method of claim 1 wherein the laser beam is energized in a repetitive pulse mode and the cooling means is applied between the laser pulses.

5. The method of claim 4 wherein said cooling means is a inert gas.

6. The method of claim 5 wherein said inert gas is generated from liquid nitrogen.

7. The method of claim 1 wherein said radiation delivery system is a fiber optic system.

8. The method of claim 1 wherein the fingernails are coated.

9. The method of claim 8 wherein a design is generated on said coating.

10. The method of claim 8 wherein said coating comprises a fingernail lacquer.

11. A method for cutting or sculpting fingernails of a person comprising the steps of:
   (a) securing at least one finger of said person having a fingernail portion onto a suitable hand template;
   (b) positioning a laser directing means including an articulate arm assembly containing a laser over the desired fingernail target site; and
   (c) selectively energizing a laser beam of sufficient intensity to produce the desired cutting or to score the fingernail itself in a sculpting procedure.

12. The method of claim 11 including cooling said target site.

13. The method of claim 11 including the step of pre-soaking said fingernail with water before cutting or sculpting.

14. The method of claim 13 wherein said laser beam is generated from a carbon dioxide laser.

15. The method water of claim 11 including the step of providing a protective coating prior to laser cutting.

16. A method for decorating fingernails of a person comprising the step of:
   a) coating said fingernails with at least one colored coating;
   b) providing a name for controlling movement of a laser to follow a preselected design;
   c) monitoring temperature of the fingernail site; and
   d) energizing a laser beam of sufficient intensity to melt said coating so as to impart a design without cutting said fingernail.

* * * * *